(12) United States Patent
Sahoo

(10) Patent No.: US 11,998,634 B2
(45) Date of Patent: Jun. 4, 2024

(54) MICRO- OR NANO EMULSIONS INCLUDING ANTICANCER DRUGS

(71) Applicant: CAPNOPHARM GMBH, Tübingen (DE)

(72) Inventor: Ranjita Sahoo, Goch (DE)

(73) Assignee: CAPNOPHARM GMBH, Tübingen (DE)

( * ) Notice: Subject to any disclaimer, the term of this patent is extended or adjusted under 35 U.S.C. 154(b) by 274 days.

(21) Appl. No.: 17/414,065

(22) PCT Filed: Dec. 6, 2019

(86) PCT No.: PCT/EP2019/083938
§ 371 (c)(1),
(2) Date: Jun. 15, 2021

(87) PCT Pub. No.: WO2020/126539
PCT Pub. Date: Jun. 25, 2020

(65) Prior Publication Data
US 2022/0054413 A1 Feb. 24, 2022

(30) Foreign Application Priority Data

Dec. 19, 2018 (EP) .................................. 18213995

(51) Int. Cl.
| | | |
|---|---|---|
| *A61K 9/107* | (2006.01) | |
| *A61K 31/12* | (2006.01) | |
| *A61K 31/282* | (2006.01) | |
| *A61K 31/337* | (2006.01) | |
| *A61K 31/704* | (2006.01) | |
| *A61K 33/243* | (2019.01) | |
| *A61K 47/10* | (2017.01) | |
| *A61K 47/14* | (2017.01) | |
| *A61K 47/26* | (2006.01) | |

(52) U.S. Cl.
CPC .............. *A61K 9/107* (2013.01); *A61K 31/12* (2013.01); *A61K 31/282* (2013.01); *A61K 31/337* (2013.01); *A61K 31/704* (2013.01); *A61K 33/243* (2019.01); *A61K 47/10* (2013.01); *A61K 47/14* (2013.01); *A61K 47/26* (2013.01)

(58) Field of Classification Search
CPC ...... A61K 9/107; A61K 31/12; A61K 31/282; A61K 31/337; A61K 31/704; A61K 33/243; A61K 47/10; A61K 47/14; A61K 47/26; A61K 9/1075; A61K 9/0019
See application file for complete search history.

(56) References Cited

U.S. PATENT DOCUMENTS 6,348,491 B1 * 2/2002 Chu ..................... A61K 47/10
514/76
6,440,437 B1 * 8/2002 Krzysik ................ A61Q 19/00
424/443

FOREIGN PATENT DOCUMENTS

CN 104706585 A 6/2015
WO WO-2012104262 A1 * 8/2012 ............... A61K 8/11

OTHER PUBLICATIONS

International Search Report and Written Opinion dated Jan. 31, 2020 for corresponding PCT Application No. PCT/EP2019/083938.
Vivek Borhade et al., "Clotrimazole nanoemulsion for a malaria chemotherapy. Part 1: Preformulation studies, formulation design and physicochemical evaluation," International Journal of Pharmaceutics, vol. 431, No. 1, 2011, pp. 138-148 XP028921886.
Abhijit A. Date et al., "Design and evaluation of self-nanoemulsifying during delivery systems (SNEDDS) for cefpodoxime proxetil," International Journal of Pharmaceutics, vol. 329, No. 1-2, 2006, pp. 166-172 XP005809188.

\* cited by examiner

*Primary Examiner* — Robert A Wax
*Assistant Examiner* — Quanglong N Truong
(74) *Attorney, Agent, or Firm* — POLSINELLI PC

(57) ABSTRACT

The invention relates to new emulsion formulations comprising polyethylene glycol (15)-hydroxystearate, polyglyceryl-3 oleate and one, two, three or more anti-cancer drugs as well as such emulsion formulations for use in the treatment of cancer and a method for producing such emulsion formulations. Preferably, the emulsion formulation can further comprise one or more immunomodulatory drugs or adjuvant.

20 Claims, No Drawings

MICRO- OR NANO EMULSIONS INCLUDING ANTICANCER DRUGS

CROSS-REFERENCE TO RELATED APPLICATIONS

This application is a national stage application (under 35 U.S.C. § 371) of PCT/EP2019/083938, filed Jun. 12, 2019, which claims benefit of European Application No. 18213995.6, filed Dec. 19, 2018, which are incorporated herein by reference in their entireties.

The present invention relates to new emulsion formulations, such formulations for use in the treatment of cancer and a method for producing such emulsion formulations.

Cancer is the second leading cause of death globally, and is responsible for an estimated 9.6 million deaths in 2018. Globally, about 1 in 6 deaths is due to cancer. Among the most common cancers are lung cancer (2.09 million cases, 1.76 million deaths in 2018), breast cancer (2.09 million cases, 627,000 deaths in 2018), colorectal cancer (1.80 million cases, 862,000 deaths in 2018), prostate cancer (1.28 million cases) and stomach cancer (1.03 million cases, 783,000 deaths in 2018).

Metastases are new pathological sites spread by a cancerous (e.g. malignant) tumour. Malignant tumours are capable to invade into adjacent and distant tissue, e.g. by invasion into the blood circulation, followed by invasion into another site, where another tumour (i.e. a metastasis) may grow. Likewise, such tumours may spread along various tissues, which complicates especially a surgical removal of the tumour.

The cancer site as used herein is the part or cavity of the body, i.e. the respective tissue or part of a tissue, where cancer cells located.

Particularly in view of cancer sites, the abdomen is an important region of the body. The abdomen stretches from the thorax at the thoracic diaphragm to the pelvis at the pelvic brim. The region occupied by the abdomen is termed the abdominal cavity and contains many organs such as the stomach, the small intestine and the colon, the liver, the gall bladder and the pancreas. The abdominal cavity is coated by an extensive membrane, called the peritoneum, which covers the abdominal wall and the pelvic walls (parietal peritoneum) as well as the included organs (visceral peritoneum).

A special form of metastases are abdominal, particularly peritoneal metastases. As the cancer cells are attached to the outside of several organs and tissues but reach into the area of the peritoneum (and are thus classified as abdominal or particularly peritoneal), these metastases are more difficult to reach with medication via the blood circulation. Cancer cells may therefore "escape" into the peritoneum and/or peritoneal cavity. Still, in many cases, these cancer sites are covered by the peritoneum, i.e. are positioned between the respective organ or tissue and the peritoneum.

The terms "peritoneal metastasis" and "peritoneal cancer" as used herein may be understood as synonyms. Both terms comprise cancer cells of a primary or a secondary site of the host's body.

The treatment options for cancer strongly depend on several factors such as the involved organs, the cause of cancer and further complicating factors as well as the age and health status of the patient.

Although many limitations, for various cancer types, a systemic chemotherapy is applied as a standard of care. However, several tissues have a poor vascularisation and can thus be poorly reached by a systemically applied chemotherapy. The therapy thus results in a poor performance. As a counteractive measure, higher doses and/or higher volumes of the chemotherapeutic agent(s) could be applied transport higher amounts of the chemotherapeutic agent into the poorly vascularised tissues. However, increasing concentrations also increase the risk of dangerous adverse effects, renal toxicity, neurotoxicity or cardiac toxicity.

As an improvement to systemic chemotherapy, local chemotherapy can be applied to patients with tumour sites in poorly vascularized tissues. The delivery of the chemotherapeutically active substance is thereby localised to a desired tissue or region.

Such treatment options have recently emerged particularly for cancer sites in the poorly vascularized peritoneal cavity:

Possible treatment options for peritoneal metastasis are e.g. Hyperthermic Intraperitoneal Chemotherapy (HIPEC) or Pressurized Intraperitoneal Aerosol Chemotherapy (PIPAC).

Hyperthermic Intraperitoneal Chemotherapy (HIPEC) is a treatment usually performed after surgery when all visible cancer sites in the abdomen are surgically removed. A liquid heated chemotherapy is applied to the peritoneal cavity, bathing all reachable organs and their surfaces. With this treatment, any remaining cancer cells shall be killed. However, this treatment is a time-consuming process with higher mortality rates.

Pressurized Intraperitoneal Aerosol Chemotherapy (PIPAC) is a palliative treatment of peritoneal metastasis. PIPAC is a drug delivery system applying chemotherapeutic drugs, in form of an aerosol, under pressure into the abdominal cavity. The aerosol is usually applied within the closed abdominal cavity, i.e. during a laparoscopy. PIPAC is a significantly time saving therapy compared to other available techniques like HIPEC.

The treatment options for such tissues, however, still face several difficulties to be solved in view of an efficient and tolerated therapy. As many cancer sites are covered by structures, e.g. the peritoneum in the abdominal cavity, which forms a complex barrier, even a localized therapy with an amount of chemotherapeutically active agent(s), which is sufficient for tumour treatment per se, faces a limited provision of the agent to the respective cancer site. Again, higher doses of the agent(s) may be used, however, have to stay within the clinically approved limits. Furthermore, higher doses frequently increase the risk of dangerous adverse effects and toxicity for the nearby tissue. As the applied doses are already sufficient for tumour treatment, a further increase of the dose will provide a high risk for the tissue covered with the agent and outside the barrier.

Therefore, the primary object of the present invention was to provide new and improved therapy options for patients suffering from cancer, particularly with (a) cancer site(s) at hardly reachable tissues and corresponding (pharmaceutical) formulations.

The primary object is achieved by an emulsion formulation, comprising or consisting of
  a) polyethylene glycol (15)-hydroxystearate,
  b) polyglyceryl-3 oleate,
  c) one, two, three or more anti-cancer drugs, and
  d) optionally: polysorbate, preferably polysorbate 80,
wherein the emulsion is an oil-in-water micro- or nanoemulsion.

Such formulation has an oil phase and a water phase, preferably wherein the oil phase comprises components a), b) and c) and the water phase comprises component d).

An oil-in-water emulsion is an emulsion, wherein the oil is the dispersed phase, and water is the dispersion medium. Whether an emulsion of oil and water turns into an oil-in-water or water-in-oil emulsion depends on the volume fraction of the respective phases and, if present, the type of emulsifier.

The formulations according to the present invention are particularly useful in the treatment of cancer, preferably a cancer type selected from the group consisting of gastrointestinal cancer, gynaecological cancer, prostate cancer, peritoneal metastasis, leukemia, lymphoma, soft-tissue sarcoma, pseudomyxoma peritonei, yolk sack tumor, peritoneal cancer, multiple myeloma, breast cancer, bladder cancer, lung cancer, thyroid cancer, Kaposi's sarcoma, particularly preferably ovarian cancer, peritoneal metastasis colorectal cancer or stomach cancer and other cancers.

Consequently, the present invention also relates to corresponding formulations according to the present invention as described herein for use in the treatment of cancer, preferably a cancer type selected from the group consisting of gastrointestinal cancer, gynaecological cancer, prostate cancer, peritoneal metastasis, leukaemia, lymphoma, soft-tissue sarcoma, multiple myeloma, breast cancer, bladder cancer, lung cancer, thyroid cancer, Kaposi's sarcoma, particularly preferably ovarian cancer, peritoneal metastasis colorectal cancer or stomach cancer.

In current therapies, the anti-cancer drugs are used in form of a solution for all application forms. However, it was found that emulsions, particularly according to the invention, provide several advantages. Emulsions according to the invention were found to provide a better therapeutic drug delivery, as these may pass more easily the barriers, such as e.g. the peritoneum, in the organism and thus an enhanced e.g. peritoneal permeation can be obtained. Furthermore, the emulsions have an increased long-term stability and safety record and are suitable for active substances, such as anti-cancer drugs, which are poorly soluble, have a low bioavailability or a narrow therapeutic index. The emulsions also protect the active substance, such as the anti-cancer drug, from enzymatic degradation and hydrolysis. Due to their higher viscosity compared to aqueous solutions and due to their higher surface adhesion forces, emulsion preferably provide a longer contact time of the therapeutic substance with the target tissue as compared to aqueous solutions.

In this way, a higher amount of drugs or combinations of drugs can be delivered to the target region, resulting in a higher effect of the therapy, which may prolong the survival of a patient and preserve his quality of life. Furthermore, as the delivery is increased, a lower amount of drug in total can be applied. Lower doses of drugs avoid adverse effects or decrease their severity. Thus, a safe and effective drug delivery is provided by the emulsions according to the invention.

It was surprisingly found that the combination of polyethylene glycol (15)-hydroxystearate and polyglyceryl-3 oleate provided advantageous effects for the characteristics of the emulsion formulation. These effects comprise the promotion and/or provision of a homogeneous dispersion when polyethylene glycol (15)-hydroxystearate and polyglyceryl-3 oleate are used. Furthermore, the emulsion droplets can be obtained in a nanometer range, i.e. a mean diameter in a nanometer range. With polyethylene glycol (15)-hydroxystearate and polyglyceryl-3 oleate, a bluish tinge dispersion is obtained, which indicates a monodisperse dispersion. Furthermore, it was surprising that by using polyethylene glycol (15)-hydroxystearate and polyglyceryl-3 oleate only low effort is needed to be made for homogenizing a prepared formulation according to the invention. Nevertheless, a homogenisation step may be applied to further enhance the stability and dispersability of the obtained mixture. The obtained mixture was already homogenised at low pressure. Surprisingly, the obtained mixtures were homogenised already after application of 1500 bar, preferably already after application of 800 bar, particularly preferably already after application of 500 bar, especially preferably after application of 200 bar. Preferably, the pressure is applied via or within a homogenizer, preferably a continuous or discontinuous homogenizer, particularly preferably a discontinuous homogenizer. Preferably, a pressure of 800 bar, 500 bar or 200 bar is applied in 2 or 3 cycles, or a pressure of 1500 bar is applied in 2 cycles. A cycle in this regard describes the step in which the mixture to be homogenized is passed through the homogenizer. Likewise, the emulsion formulation according to the invention was thus more stable than other emulsion formulations.

The stability of an emulsion refers to its ability to resist changes in its properties, particularly its homogeneity, over time. Such changes may occur in form of a fusion of the droplets in the emulsion due to attractive forces or due to a higher density of the droplets compared to the dispersion medium, because of which the droplets will sink down and aggregate. A fusion of the droplets may thus result in a heterogeneous mixture, which is no longer an emulsion.

Compared to conventional emulsions, the emulsions according to the invention provide several advantages: Usually, the emulsions according to the invention are a bluish tinge transparent dispersion, which are present as a monodispersed phase, whereas conventional emulsions are white dispersions which are present as a polydispersed phase. Furthermore, the emulsions according to the invention have a higher dilution potential compared to conventional emulsions. Additionally, emulsions according to the invention are more stable than conventional emulsions, which typically show limited stability. Furthermore, conventional emulsions are often only suitable for a specific route of administration, which depends on the precise recipe and composition of the emulsion. Therefore, the production of a conventional emulsion needs to be adapted for each recipe and is often very specific for only one emulsion. On the contrary, the emulsions according to the invention are suitable for diverse routes of application and can furthermore be easily produced by methods as described herein.

Polyethylene glycol (15)-hydroxystearate is also known as Macrogol (15)-hydroxystearate or Polyoxyethylated 12-hydroxystearic acid and is represented by the following formula (Formula I), wherein in case of any non-conformances the compound represented by the chemical formula is referred to herein, wherein n is an integer.

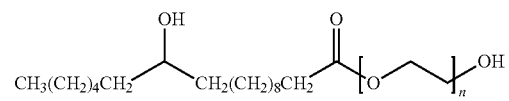

(Formula I)

Polyglyceryl-3 oleate is represented by the following formula (Formula II), wherein in case of any non-conformances the compound represented by the chemical formula is referred to herein.

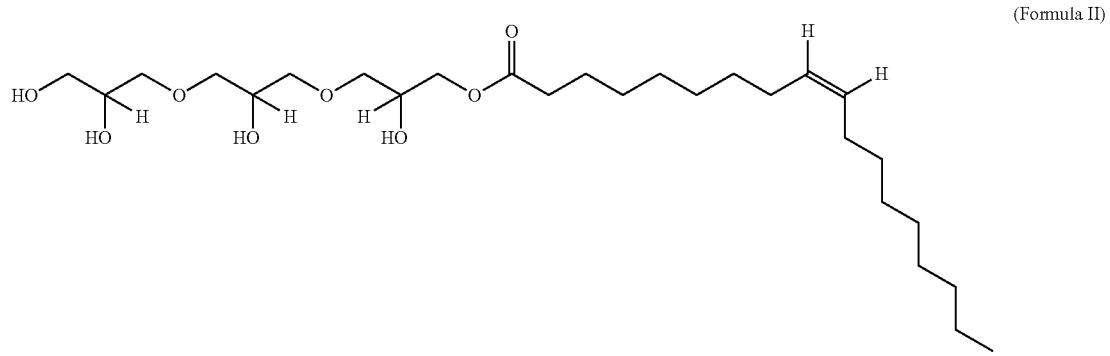 [SMILES: CCCCCCCC/C=C\CCCCCCCC(=O)OCC(O)COCC(O)COCC(O)CO]
(Formula II)

Anti-cancer drugs as described herein are drugs comprising at least one anti-cancer ingredient, wherein the ingredient has an anti-cancer effect, effective in the treatment of benign and/or malignant cancer cells.

Exemplary anti-cancer drugs are cisplatin, doxorubicin, oxaliplatin and paclitaxel.

Cisplatin is a known anti-cancer drug, which is often used in the treatment of testicle carcinoma, ovarian carcinoma, bronchial carcinoma, bladder carcinoma, cervical carcinoma, squamous cell carcinoma at the head and neck as well as choriocarcinoma. Typically, cisplatin is used in combination with other anti-cancer drugs, which is also preferred with regard to the present invention. Further and according to the invention, cisplatin is preferably used in the treatment of tumours as typically for cisplatin. The typically applied concentration of cisplatin is 1 mg/1 ml of solution.

Doxorubicin is a known anti-cancer drug, which is often sued in the treatment of mammary carcinoma, bronchial carcinoma and lymphoma. According to the invention, doxorubicin is preferably used in the treatment of tumours as typically for doxorubicin. The typically applied concentration of doxorubicin is 10 mg/1 ml of solution.

Oxaliplatin is a known anti-cancer drug, which is often used in the treatment of colon carcinoma and colorectal carcinoma. Typically, oxaliplatin is used in combination with 5-fluorouracil and/or folinic acid. In light of the present invention, such combinations are preferred to be used. Further and according to the invention, oxaliplatin is preferably used in the treatment of tumours as typically for oxaliplatin. The typically applied concentration of oxaliplatin is 5 mg/1 ml of solution.

Paclitaxel is a known anti-cancer drug, which is often used in the treatment of ovarian carcinoma, mammary carcinoma, non-small cell bronchial carcinoma, adenocarcinoma of the pancreas and prostate cancer. Typically, paclitaxel is used in combination with cisplatin, carboplatin, trastuzumab and/or gemcitabin. Paclitaxel is preferably used in the treatment of tumours as typically for paclitaxel. The typically applied concentration of paclitaxel is 6 mg/1 ml of solution.

Usually and thus preferably, the emulsion formulation according to the present invention includes a component e) which is one or more further substances, particularly preferably one or more pharmaceutically acceptable substances.

Pharmaceutically acceptable substances as described herein may for example be oils, co-solvents, surfactants, such as hydrophilic surfactants, viscosity modifiers, polysaccharides, isotonicity agents, pH modifiers.

Preferably, component e) comprises or consists of immunomodulatory drugs, such as curcumin, lutein, hesperidin, apigenin, hesperetin, aioene, arctigenin, 6-carotene, epigallocatechin-3-gallate, ginsan, glabridin and guinic acid. If component e) comprises or consists of immunomodulatory drugs, it is further preferred that these immunomodulatory drugs are present in a concentration of 1 to 10 wt.-% each or in sum, related to the emulsion formulation.

Depending on the application of the emulsion formulation, component e) can also be TPGS, one or more vitamin(s), one or more salt(s) and/or one or more ions.

It is preferred that the emulsion formulation comprises one anti-cancer drug but no immunomodulatory drug.

It is also preferred that the emulsion formulation comprises two or more anti-cancer drugs but no immunomodulatory drug.

Moreover, it is preferred that the emulsion formulation comprises one anti-cancer drug and one immunomodulatory drug.

It is also preferred that the emulsion formulation comprises one anti-cancer drug and two or more immunomodulatory drugs.

Furthermore, it is preferred that the emulsion formulation comprises two or more anti-cancer drugs and one immunomodulatory drug.

Further, it is also preferred that the emulsion formulation comprises two or more anti-cancer drugs and two or more immunomodulatory drugs.

A microemulsion as described herein is preferably an emulsion wherein the particles in average (mean particle size) have a diameter of 1000 to 100 nm.

A nanoemulsion as described herein is preferably an emulsion wherein the particles in average (mean particle size) have a diameter of less than 100 nm.

The measurement of the geometrical dimensions (e.g. the diameter) of the particles and the size distribution profile as well as the mean particle size can be performed by any suitable method, such as e.g. photon correlation spectroscopy and laser diffraction. Preferably, in the context of the present invention the mean particle size is determined by using a particle size analyser (e.g. N5 Beckman submicron particle size analyser), for example at a fixed angle of 90° at 20° C., wherein preferably double distilled water can be used as dispersant.

Preferably, the amount of polyethylene glycol (15)-hydroxystearate in the formulation is in a range of from 0.25 to 15 wt.-%, preferably in a range of from 0.5 to 10 wt.-%, particularly preferably in a range of from 0.75 to 7.5 wt.-%, especially preferably in a range of from 0.75 to 5 wt.-%, related to the total weight of the formulation.

Additionally, or alternatively, it is preferred that the amount of polyglyceryl-3 oleate in the formulation is in a range of from 0.05 to 10 wt.-%, preferably in a range of from 0.1 to 5 wt.-%, particularly preferably in a range of from 0.1 to 2 wt.-%, especially preferably in a range of from 0.2 to 2 wt.-%, related to the total weight of the formulation.

It is preferred that the weight ratio of compound a) to compound b) is in a range of from 0.25 to 25, preferably in a range of from 0.5 to 20, particularly preferably in a range of from 1 to 15, especially preferably in a range of from 2 to 10.

Preferably, the or, respectively, at least one of the anti-cancer drugs is oxaliplatin, preferably wherein the amount of oxaliplatin in the formulation is in a range of from 0.001 to 1.75 wt.-%, preferably in a range of from 0.005 to 1.5 wt.-%, particularly preferably in a range of from 0.01 to 1.5 wt.-%, related to the total weight of the formulation.

Additionally or alternatively, it is preferred that the or, respectively, at least one of the anti-cancer drugs is cisplatin, preferably wherein the amount of cisplatin in the formulation is in a range of from 0.0005 to 1.5 wt.-%, preferably in a range of from 0.001 to 1.5 wt.-%, particularly preferably in a range of from 0.005 to 1.25 wt.-%, related to the total weight of the formulation.

Additionally or alternatively, it is preferred that the or, respectively, at least one of the anti-cancer drugs is doxorubicin, preferably wherein the amount of doxorubicin in the formulation is in a range of from 0.0001 to 5 wt.-%, preferably in a range of from 0.0005 to 4 wt.-%, particularly preferably in a range of from 0.001 to 3.0 wt.-%, especially preferably in a range of from 0.00005 to 2.5 wt.-%, related to the total weight of the formulation.

Additionally or alternatively, it is preferred that the or, respectively, at least one of the anti-cancer drugs is paclitaxel, preferably wherein the amount of paclitaxel in the formulation is in a range of from 0.00005 to 2 wt.-%, preferably in a range of from 0.00001 to 2 wt.-%, particularly preferably in a range of from 0.0005 to 2 wt.-%, related to the total weight of the formulation.

Preferably, the term "at least one", as used herein, means 1, 2, 3, 4 or 5.

In case one or more further substances, preferably one or more pharmaceutically acceptable substances are present (component e)), it is preferred that they are present in an amount of up to 99.60005 wt.-%, related to the total weight of the formulation.

It is further preferred that the average particle size of the oil-in-water emulsion is in a range of from 10 to 1000 nm, preferably in a range of from 20 to 800 nm.

Further preferably, the emulsion formulation is a liquid or an aerosol. In a preferred embodiment, the emulsion formulation is a liquid or an aerosol at least under standard conditions, which are 20° C. and 1013 mbar. As described herein, the emulsion formulation is preferably applied via a laparoscopic nebulizer, wherein after application, the emulsion is in aerosolized form.

The term "liquid", as used herein, includes liquids as well as viscous and semi-viscous fluids.

The term "aerosol", as used herein, preferably describes a mixture of liquid droplets in air or another gas or gas mixture.

It is preferred that the emulsion formulation is administered by systemic or local application, wherein as systemic application, an oral, or intravenous application is preferred, and wherein as local application, an intraperitoneal application is preferred.

A systemic application, as used herein, describes an application with which the active substance(s), e.g. the anti-cancer drug, is/are administered into the blood and/or lymph system and thus a distribution over the whole body, at least the parts which are not separated by barriers (such as the blood brain barrier) is made possible. The distribution may be achieved directly (e.g. by intravenous injection) or indirectly (e.g. by oral application).

A local application, as used herein, includes applications where the active substance(s) is/are administered onto/into the tissue in which an effect is desired, or a tissue nearby.

Such applications include for example intramuscular injections or an intraperitoneal application.

With regard to the application, it is further preferred that the emulsion formulation is administered with an assisting tool selected from the group consisting of microneedles, catheters, spray devices, angio-injectors, or any combination thereof, preferably with a nebulizer, spraying gun or spray catheter, especially preferably with a laparoscopic nebulizer, such as the laparoscopic nebulizer known as Capnopen, preferably as described in U.S. Pat. No. 9,511,197 B2.

The present invention also relates to a method for producing an emulsion formulation, preferably an emulsion formulation according to the invention, comprising or consisting of the following steps:
  providing polyethylene glycol (15)-hydroxystearate,
  providing polyglyceryl-3 oleate,
  providing the anti-cancer drug(s),
  optionally, providing further components,
  adding the provided components to each other, and
  optionally: homogenising the provided compounds.

In case one or more further substances, preferably one or more pharmaceutically acceptable substances are present (component e)), this/these is/are preferably provided before the adding step and added before, during or after the adding step described above.

In case the components a) to d) or, respectively, e) do not add up to 100 wt.-%, water may be added to fill up to 100 wt.-%. Depending on e.g. the form of application or the amount of treatments, the emulsion formulations can preferably be applied in further diluted form, for which a diluent, preferably water, may be added.

Preferably, the homogenising step is performed at a temperature in a range of from 50 to 80° C., particularly preferably from 50 to 60° C.

Additionally, or alternatively, it is preferred that the homogenisation step is performed by using low shear mixing, preferably at 500 to 2,000 rpm. Preferably up to 3 cycles of homogenization are applied afterwards and at a pressure of 200 to 500 bar. Particularly preferably, 3 cycles at 200 bar or 3 cycles at 500 bar are applied. Further preferably, only 2 cycles of homogenization at 1000 bar are applied.

Additionally, or alternatively, it is preferred that the homogenisation step is performed by using medium shear mixing, preferably at 2000 to 10,000 rpm. Preferably up to 3 cycles of homogenization are applied afterwards and at a pressure of 200 to 500 bar, especially preferably 3 cycles at 500 bar are applied. Particularly preferably, only 2 cycles of homogenization at 1000 bar are applied.

Additionally or alternatively, it is preferred that the homogenisation step is performed by using high shear mixing, preferably at 10,000 to 30,000 rpm. Preferably up to 3 cycles of homogenization are applied afterwards and at a pressure of 200 to 500 bar, especially preferably 3 cycles at 200 bar are applied. Particularly preferably, only 2 cycles of homogenization at 1000 bar are applied.

Additionally or alternatively, it is preferred that the homogenisation step is performed by using high pressure homogenisation, preferably with a first step performed at 500 to 2,000 rpm and a second step performed as up to 3 cycles of homogenization at a pressure of 200 to 500 bar, preferably 3 cycles at 200 bar or preferably 3 cycles at 500 bar. Particularly preferably, only 2 cycles of homogenization at 1000 bar are applied.

The homogenisation step may be performed by using/applying magnetic stirring, an ultra turrax, microfluidisation, ultrasonication, jet streaming, high shear medical device cavities or any other suitable disruptive technology.

The process for preparing a formulation according to the invention may further comprise the step of heating up the oil and/or water phase to 50 to 80° C., preferably to 50 to 60° C. Furthermore, the phases are mixed and/or homogenized as described above and stored at the heated temperature for 10 to 40 min, preferably for 15 to 30 min, particularly preferably for 20 to 25 min.

In a preferred embodiment, the homogenising step, if present, may also be applied simultaneously with the adding step. As an example, and thus not limited thereto, the provided components may be added slowly or piece by piece and the mixture obtained little by little is constantly homogenised. The term "simultaneously" as used in this special regard is meant to be understood such that the adding step and the homogenising step, both as a whole, are essentially performed within the same time. Therefore, the adding step may be initiated before the homogenising step and/or the homogenising step may be terminated after the last component has been added. Preferably in this regard, the term "piece by piece" is meant to be understood such that also a provided component itself can be added piece by piece. Furthermore, pieces of the provided components can also be added alternatingly, i.e. a provided component does not need to be fully added before another (piece of) component can be added.

Preferably, the emulsion formulation according to the invention is prepared or preparable by a method according to the invention.

According to a preferred embodiment of the present invention, the emulsion formulation is produced by the method described herein and is a micro- or nanoemulsion as described herein.

Also described herein is a method of treatment of a cancer patient, preferably a patient suffering from a cancer type selected from the group consisting of gastrointestinal cancer, gynaecological cancer, prostate cancer, peritoneal metastasis, leukemia, lymphoma, soft-tissue sarcoma, pseudomyxoma peritonei, yolk sack tumor, peritoneal cancer, multiple myeloma, breast cancer, bladder cancer, lung cancer, thyroid cancer, Kaposi's sarcoma, particularly preferably ovarian cancer, peritoneal metastasis of colorectal cancer or stomach cancer, wherein the method comprises or consists of the following steps:

administering an emulsion formulation, preferably an emulsion formulation according to the invention, to a patient in need thereof, preferably in an amount sufficient for treating the cancer.

Preferably and thus not limited thereon, the sufficient amount for treating the cancer can be an amount sufficient for slowing down or preventing cancer growth and/or cancer cell division, for inhibiting angiogenesis, for antihormone therapy, for cancer immunotherapy or for palliative care.

What was said with regard to the formulations according to the present invention can also be applied to preferred embodiments of the above-described method.

When treating a patient suffering from cancer, preferably a cancer type as described above, with an emulsion formulation as described above, the physician may apply the emulsion formulation systemically or locally. For a systemic application, often an infusion or an injection into the blood system is applied. For a local application, the physician may either inject the emulsion formulation into the tissue to be treated or a tissue nearby. In some cases, an intraperitoneal application may be desired. In this case, a physician may use e.g. a laparoscopic nebulizer as e.g. the Capnopen® as described in U.S. Pat. No. 9,511,197 B2, which is inserted into the peritoneum with its front part. By inserting the emulsion formulation in form of an aerosol, a volume of about 200 ml is applied, e.g. sprayed into the peritoneum. Thus, the peritoneum is inflated, which allows the inserted aerosol and thus the emulsion formulation to cover all or big areas of the peritoneum itself. After inserting and exposure, the gas part of the aerosol, e.g. $CO_2$ is released or mechanically removed from the peritoneum, wherein the emulsion formulation is applied onto the desired but hardly reachable tissue with currently available treatment procedures. This treatment is usually repeated once, twice or three times, each six weeks after the last treatment.

Preferred embodiments and further aspects of the present invention emerge from the attached patent claims and the following examples, wherein the present invention is not limited to these examples.

EXAMPLES

Example 1: Emulsion Formulation 1

| Ingredient | Amount [wt.-%] |
| --- | --- |
| Polyethylene glycol (15)-hydroxystearate | 5 |
| Polyglyceryl-3 oleate | 1 |
| Oxaliplatin | 0.1 |
| Soybean oil | 6 |
| Poloxamer (10% solution) | 10 |
| Water | Ad 100 |
| Sum | 100 |

The ingredients were provided and slowly added one after the other into the provided water. During the adding step, the mixture was constantly homogenised by magnetic stirring at 1200 rpm. In total, the mixture was stirred for 10 min. The homogenisation step was performed at 60° C. at 1000 bar 2 cycles.

Mean particle size and particle size distribution of the emulsion formulation were analysed using a N5 Beckman submicron particle size analyser at a fixed angle of 90° at 20° C. in double distilled water as dispersant.

The obtained results are shown below:

Mean particle size: 180 nm

Particle size distribution: The particle size ranged from 50 to 500 nm.

Example 2: Emulsion Formulation 2

| Ingredient | Amount [wt.-%] |
| --- | --- |
| Polyethylene glycol (15)-hydroxystearate | 3 |
| Polyglyceryl-3 oleate | 1 |
| Cisplatin | 0.05 |

-continued

| Ingredient | Amount [wt.-%] |
|---|---|
| Olive oil | 6 |
| Poloxamer (10% solution) | 10 |
| Water | Ad 100 |
| Sum | 100 |

The ingredients were provided and slowly added one after the other into the provided water. The mixture was homogenised by using an ultra turrax at 20,000 rpm for 5 min. The homogenisation step was performed at 60° C. and at 200 bar 3 cycles.

Mean particle size and particle size distribution of the emulsion formulation were analysed using a N5 Beckman submicron particle size analyser at a fixed angle of 90° at 20° C. in double distilled water as dispersant.

The obtained results are shown below:
Mean particle size: 310 nm
Particle size distribution: The particle size ranged from 50 to 700 nm.

Example 3: Emulsion Formulation 3

| Ingredient | Amount [wt.-%] |
|---|---|
| Polyethylene glycol (15)-hydroxystearate | 3 |
| Polyglyceryl-3 oleate | 1 |
| Paclitaxel | 0.1 |
| Medium chain triglycerides | 6 |
| Poloxamer (10% solution) | 10 |
| Water | Ad 100 |
| Sum | 100 |

The ingredients were provided and slowly added one after the other into the provided water. The mixture was homogenised by magnetic stirring at 1200 rpm for 2 min at 60° C. Afterwards the mixture was further homogenised for 2 cycles at 500 bar.

Mean particle size and particle size distribution of the emulsion formulation were analysed using a N5 Beckman submicron particle size analyser at a fixed angle of 90° at 20° C. in double distilled water as dispersant.

The obtained results are shown below:
Mean particle size: 110 nm
Particle size distribution: The particle size ranged from 20 to 150 nm Example 4: Increased Delivery An emulsion according to the invention was prepared according to Example 1, additionally comprising curcumin. Further, a conventional emulsion comprising curcumin was provided.

Both emulsions were sprayed into an inverted cow bladder tissue with the laparoscopic nebulizer known as Capnopen.

The cow bladder tissue was subsequently analysed for the penetration of the emulsions via fluorescence microscopy, wherein the autofluorescent curcumin was detected.

For the emulsion according to the invention, the depth of penetration into the tissue was much higher than the depth for the conventional emulsion.

The invention claimed is:

1. An emulsion formulation comprising:
   (a) 1 to 15 wt. % of polyethylene glycol (15)-hydroxystearate,
   (b) 0.3 to 10 wt. % of polyglyceryl-3 oleate,
   (c) at least one anti-cancer drug selected from oxaliplatin, cisplatin, doxorubicin, or paclitaxel,
   (d) optionally, polysorbate, and
   (e) water,
   wherein the emulsion is an oil-in-water micro- or nanoemulsion and all percentages by weight are based on a total weight of the emulsion formulation.

2. The emulsion formulation according to claim 1, wherein (a) and (b) are in a weight ratio of 1:1 to 15:1 ((a):(b)).

3. The emulsion formulation according to claim 1, wherein the at least one anti-cancer drug is oxaliplatin in an amount of 0.005 to 1.5 wt. %, cisplatin in an amount of 0.001 to 1.5 wt. %, doxorubicin in an amount of 0.001 to 3.0 wt. %, paclitaxel in an amount of 0.00001 to 2 wt. %, or a combination thereof.

4. The emulsion formulation according to claim 1, wherein the average particle size of the oil-in-water emulsion is from 10 to 1000 nm.

5. The emulsion formulation according to claim 1, wherein the formulation is a liquid or an aerosol.

6. The emulsion formulation according to claim 1, wherein the formulation is prepared by or producible by a process comprising:
   providing the polyethylene glycol (15)-hydroxystearate,
   providing the polyglyceryl-3 oleate,
   providing the at least one anti-cancer drug,
   optionally, providing further components,
   adding the provided components to each other, and
   optionally, homogenising the provided compounds.

7. The emulsion formulation according to claim 6, wherein the homogenisation is performed:
   at 50 to 80° C., and/or
   by using low shear mixing, and/or
   by using medium shear mixing, and/or
   by using high shear mixing, and/or
   by using high pressure homogenisation.

8. A method for preparing the emulsion formulation of claim 1 comprising:
   providing polyethylene glycol (15)-hydroxystearate,
   providing polyglyceryl-3 oleate,
   providing the at least one anti-cancer drug,
   optionally, providing further components,
   adding the provided components to each other, and
   optionally, homogenising the provided compounds.

9. The method according to claim 8, wherein the homogenisation is performed:
   at 50 to 80° C., and/or
   by using low shear mixing, and/or
   by using medium shear mixing, and/or
   by using high shear mixing, and/or
   by using high pressure homogenisation.

10. The method according to claim 8, wherein the homogenising is performed simultaneously with the adding.

11. A method for treating cancer in a patient suffering from cancer comprising administering the emulsion formulation according to claim 1 to the patient.

12. The method of claim 11, wherein the emulsion formulation is administered to the patient by intraperitoneal administration.

13. The method of claim 12, wherein the emulsion formulation is administered using an assisting tool chosen from microneedles, spray devices, angioinjectors, or a combination thereof.

14. The emulsion formulation according to claim 1, wherein the polyethylene glycol (15)-hydroxystearate is in an amount of from 1 to 5 wt. % and the polyglyceryl-3 oleate is in an amount of 0.3 to 1 wt. %, based on the total weight of the formulation.

15. The emulsion formulation according to claim 1, wherein the weight ratio of (a) to (b) is 2:1 to 10:1 ((a):(b)).

16. A method for treating cancer in a patient suffering from cancer comprising intraperitoneally administering to the patient an emulsion formulation comprising:
(a) 1 to 15 wt. % of polyethylene glycol (15)-hydroxystearate,
(b) 0.3 to 10 wt. % of polyglyceryl-3 oleate,
(c) at least one anti-cancer drugs selected from oxaliplatin, cisplatin, doxorubicin, or paclitaxel,
(d) optionally, polysorbate, and
(e) water,
wherein the emulsion is an oil-in-water micro- or nanoemulsion, the average particle size of the oil-in-water emulsion is from 10 to 1000 nm, and all percentages by weight are based on a total weight of the emulsion formulation.

17. The method of claim 16, wherein the emulsion formulation comprises oxaliplatin in an amount of 0.005 to 1.5 wt. %.

18. The method of claim 16, wherein the emulsion formulation comprises cisplatin in an amount of 0.001 to 1.5 wt. %.

19. The method of claim 16, wherein the emulsion formulation comprises doxorubicin in an amount of 0.001 to 3.0 wt. %.

20. The method of claim 16, wherein the emulsion formulation comprises paclitaxel in an amount of 0.00001 to 2 wt. %.

* * * * *